United States Patent [19]

Takasugi et al.

[11] Patent Number: 5,405,838
[45] Date of Patent: Apr. 11, 1995

[54] TOPICAL POWDER COMPOSITIONS CONTAINING A CYCLIC AMP DERIVATIVE

[75] Inventors: Norio Takasugi, Yachito; Eiichi Mafune, Narashino; Toshiyuki Takayasu, Kuki, all of Japan

[73] Assignee: Daiichi Pharmaceutical Co., Ltd., Tokyo, Japan

[21] Appl. No.: 766,227

[22] Filed: Sep. 27, 1991

[30] Foreign Application Priority Data

Sep. 28, 1990 [JP] Japan .................................. 2-256991

[51] Int. Cl.$^6$ ...................... A61K 31/70; C07H 19/20
[52] U.S. Cl. .................... 514/47; 536/26.13
[58] Field of Search ................. 514/47; 536/27, 26.13; 424/501

[56] References Cited

U.S. PATENT DOCUMENTS

| | | | |
|---|---|---|---|
| 3,849,553 | 11/1974 | Dea et al. | 514/47 |
| 3,860,706 | 1/1975 | Ikeda et al. | 514/47 |
| 4,369,181 | 1/1983 | Miller et al. | 514/47 |
| 4,873,227 | 10/1989 | Ikada et al. | 514/47 |

FOREIGN PATENT DOCUMENTS

| | | | |
|---|---|---|---|
| 0234854 | 9/1987 | European Pat. Off. | 514/47 |
| 0335379 | 10/1989 | European Pat. Off. | 514/47 |

OTHER PUBLICATIONS

Database: WPIL, accession No. 88-217511 [31], Derwent Publications Ltd. London, GB; & JP-A-63 154 624 (Daiichi Seiyaku K.K.).

"Polyoxyethylene Alcohols," *Merck Index*, Merck & Co., Rahway, N.J., 1983, p. 1094, Entry 7449.

"Poly(ethylene glycol)," *Aldrich Catalog/Handbook of Fine Chemicals*, Aldrich Chemical Co., Milwaukee, Wis., 1984, see pp. 906–907.

*Primary Examiner*—Johnnie R. Brown
*Assistant Examiner*—L. Eric Crane
*Attorney, Agent, or Firm*—Oblon, Spivak, McClelland, Maier & Neustadt

[57] ABSTRACT

A topical powder composition containing a cyclic AMP derivative and a water-absorptive powdery material. The topical powder composition is useful for wet dermatoses. Release of drug can be controlled.

1 Claim, No Drawings

TOPICAL POWDER COMPOSITIONS CONTAINING A CYCLIC AMP DERIVATIVE

BACKGROUND OF THE INVENTION i) Field of the Invention

The present invention relates to a topical powder composition containing a cyclic AMP (adenosine monophosphate) derivative, and more particularly to a topical powder composition containing a cyclic AMP derivative as an active ingredient, in which by adding a water-absorptive powdery material, good water-absorptive and drying properties in wet dermatoses or mucosae are achieved, stability of the cyclic AMP derivative can be improved and release of the cyclic AMP derivative can be controlled.

ii) Description of the Background Art

Conventionally, remedy for various dermal ulcers has used an ointment containing an antibiotic or antimicrobial, an enzyme and the like, a dermal cleaning liquid or powder of a water-absorptive polymer or the like, a nulnerary coating agent or the like. In particular, for a wet surface with much exudate such as dermal ulcers, an ointment having water-absorptive and drying properties is frequently used.

On the other hand, it is well-known that cyclic AMP derivatives are useful as a remedy for various dermal ulcers, as disclosed in U.S. Pat. No. 4,873,227 or European publication 0249873 A2. When such cyclic AMP derivatives are used for the remedy of various dermal ulcers, it is considered that a composition having water-absorptive and drying properties for the skin is most effective.

However, since such a composition having water-absorptive and drying properties contains water therein, there is a problem in stability with respect to drugs such as cyclic AMP derivatives which are liable to be hydrolyzed, and it is difficult to store it for a long period. Further, there is another problem in that when such a material is applied to wet dermatopathy, release of medicaments from the composition occurs quickly and cannot be controlled.

SUMMARY OF THE INVENTION

It is therefore an object of the present invention to provide a topical powder composition containing a cyclic AMP derivative in view of the problems of the known art, which is useful as the remedy for wet dermatoses such as dermal ulcers or the like, and which is capable of maintaining stability of the cyclic AMP derivative and controlling release of the same.

In accordance with one aspect of the present invention, there is provided a topical powder composition containing a cyclic AMP derivative and a water-absorptive powdery material.

In a preferred topical powder composition, the water-absorptive powder material is selected from polyethylene glycols.

The topical powder composition is obtained either by mixing the cyclic AMP derivative, the water-absorptive material and optional additives, or by heating with fluidizing a mixture of the above components and a low melting point material to a temperature higher than the melting point of the low melting point material for granulation.

DETAILED DESCRIPTION OF THE INVENTION AND PREFERRED EMBODIMENTS

The present invention will now be described in detail with reference to Examples thereof.

In view of the problems of the known art, researches for developing a topical powder composition useful for wet dermatoses have been done to find that by using a water-absorptive powdery material together with a cyclic AMP (adenosine monophosphate) derivative to obtain a topical powder composition, the cyclic AMP derivative can be maintained to be stable and be suitably released by water present in a diseased part and/or its environment, and thus the present invention has been accomplished.

That is, according to the present invention, there is provided a topical powder composition containing a cyclic AMP derivative as an active ingredient and a water-absorptive powdery material.

Examples of the cyclic AMP (c-AMP) derivative useful as the active ingredient of this invention include $N^6$-monoacyladenosine-3',5'-cyclic phosphoric acid, 2'-O-monoacyladenosine-3',5'-cyclic phosphoric acid, $N^6,2'$-O-diacyladenosine-3',5'-cyclic phosphoric acid or their 8-mercapto, 8-lower alkylthio, 8-benzylthio, 8-amino, 8-hydroxy, 8-chloro or 8-bromo substitution product, 8-benzylthioadenosine-3',5'-cyclic phosphoric acid or its $N^6$-lower alkyl substitution product, and 8-mercaptoadenosine-3',5'-cyclic phosphoric acid, among which particularly preferred ones are sodium $N^6,2'$-O-dibutyryladenosine-3',5'-cyclic phosphate (hereinafter referred to as "DBcAMP"), sodium 2'-O-butyryladenosine-3',5'-cyclic phosphate, sodium $N^6$-butyryladenosine-3',5'-cyclic phosphate, sodium adenosine-3',5'-cyclic phosphate, 8-benzylthio-$N^6$-butyryladenosine-3',5'-cyclic phosphate, and 8-benzylthioadenosine-3',5'-cyclic phosphate. These compounds can be used singly or in combination of two or more.

The water-absorptive powdery materials which are useful in this invention, which will hereinafter be referred to simply as water-absorptive materials, are those capable of absorbing the exudate and drying up the sufferred part of the skin. Examples of such materials are water-soluble or water-absorptive substances such as sucrose, starch, pectin, gelatin, sodium alginate, methylcellulose, hydroxypropylcellulose, carboxymethylcellulose, polyvinyl alcohol, polyvinyl pyrrolidone, carboxyvinyl polymer, sodium polyacrylate and polyethylne glycol, among which is preferred polyethylene glycol and in particular polyethylene glycol having an average molecular weight of 1000–8000, such as polyethylene glycol 1000, polyethylene glycol 1500, polyethylene glycol 2000, polyethylene glycol 3000, polyethylene glycol 4000, polyethylene glycol 5000, polyethylene glycol 6000, polyethylene glycol 7000, and polyehtylene glycol 8000.

The powdery materials having a low melting point which are useful in this invention, which will hereinafter be referred to simply as low melting point materials, are those which have a melting point of 30°–100° C., and preferably, 40°–80° C. Examples of such materials include waxes such as bees wax, lanolin and carnauba wax; hydrocarbons such as paraffin, ceresine and microcrystalline wax; fatty acids such as myristic acid, lauric acid, palmitic acid, stearic acid, behenic acid and 12-hydroxystearic acid; fatty acid esters such as myristyl myristate; polyethylene glycols of various molecular weights such as polyethylene glycol 6000 and polyethylne glycol 4000; polyhydric alcohols such as batyl alcohol; higher alcohols such as stearyl alcohol and cetyl alcohol; sugar alcohols such as D-glucose and D-sorbitol; surfactants such as sorbitan fatty acid esters and polyoxyethylene hydrogenated castor oil; and mixtures of them. Materials having a relatively high melting point can also be used if two or more of such materials are blended and pulverized to bring the melting point down to fall within the range of 30°–100° C. Further, the topical powder composition of the present invention may optionally contain powdery additives useful as additives for preparing ordinary topical preparations. Examples of such additives include powdery inorganic compounds such as zinc oxide, talc, kaolin, colloidal silica, titanium oxide and the like; cellulose derivatives such as methyl cellulose, sodium carboxymethyl cellulose, hydroxypropyl cellulose and the like; synthetic polymers such as polyvinyl pyrrolidone, carboxyvinyl polymer, polyvinyl alcohol and the like; and natural polymers such as sodium alginate, gelatin and the like.

In the topical powder composition of the present invention, the mixing amounts of the above-described components are not restricted in particular. However, preferably, 40 to 99.9% by weight of the water-absorptive material and 0.1 to 60% by weight of the c-AMP derivative are mixed, and, when an additive for the topical powder composition is added, the c-AMP derivative is preferably 0.1 to 59.9% by weight (hereinafter referred to simply as %). It is preferred that particles of the powdery composition of this invention have a possibly large surface area for removing the exudate of the suffered part of the skin, with preferred particle size being less than 850 $\mu$m.

The topical powder composition of the present invention can be prepared by simply mixing a c-AMP derivative, a water-absorptive material and optional additives, or by heating with fluidizing a mixture of a c-AMP derivative, a low-melting point material and a water-absorptive material to a temperature of more than the melting point of the low melting point material for granulation. For example, a mixture of a c-AMP derivative, a powdery material and a low melting point material is heated with fluidizing, rotating or vibrating thereby adhereing the powdery material and c-AMP derivative onto the particles of the melted low melting point material to form glanules. This melt granulation method can be carried out on the basis of the description disclosed in Japanese patent laid-open (Kokai) No. Sho 58- 21433. Further, the obtained particles may be coated in order to control the release of the c-AMP derivative, if necessary.

The obtained topical powder composition according to the present invention is preferably used by applying to the affected portions of dermatoses such as dermal ulcers or the like and covering them with a nonwoven fabric, absorbent cotton, a tape or the like.

The topical powder compositions of the present invention have superior water-absorptive and drying properties compared with conventional topical agents. Further, in the topical powder compositions of the present invention, the stability is improved compared with ointments in which a c-AMP derivative is dissolved or dispersed in a base having water-absorptive and drying properties, and a control of releasing of the c-AMP derivative from the base can be performed.

The present invention is described in its preferred embodiments, however, it is readily understood that the present invention is not restricted to the preferred embodiments and that various changes and modifications thereof can be made by those skilled in the art without departing from the spirit and scope of the present invention.

EXAMPLES

The present invention will now be described in detail with reference to examples, a comparative example, and test examples, and it should be understood that these embodiments are given for illustration of the invention and are not intended to be limitative therefor.

Comparative Example

Into a 100 ml beaker, 67 g of polyethylene glycol 400 and 28 g of polyethylene glycol 4000 were put and dissolved at approximately 65° C. in a mantle heater. 1 g of dextrin and 1 g of dried aluminum hydroxide gel were added to the mixture and were sufficiently dispersed while stirring the mixture for 5 minutes by using a T.K. homomixer M type (Trademark of Tokushukika Kogyo Co.). Then, 3 g of DBcAMP was added to the mixture and was dissolved in the mixture while stirring the mixture for 5 minutes by using the homomixer. The obtained mixture was cooled with water to obtain 100 g of an ointment.

Example 1

92 g of polyethylene glycol 6000 ground by a tablet grinder and forced through a 100 mesh shieve, 3 g of talc ground in the same manner as described above and shieved through a 100 mesh screen, 2 g of colloidal silica (Aerosil 200, Nippon Aerosil Co., Ltd.) and 3 g of the DBcAMP were mixed by a mixer to prepare 100 g of a topical powder composition.

Example 2

92 g of polyethylene glycol 6000 ground and forced through a 100 mesh shieve, 5 g of Aerosil 200 shieved through a 100 mesh screen and 3 g of DBcAMP were mixed to prepare 100 g of a topical powder composition.

Example 3

92 g of polyethylene glycol 6000 ground and shieved through a 100 mesh screen, 3 g of talc ground and shieved through a 100 mesh screen, 2 g of Aerosil 200, 1 g of dextrin, 1 g of dried aluminum hydroxide gel and 3 g of DBcAMP were mixed to prepare 100 g of a topical powder composition.

Example 4

Procedures of Example 1 were followed using 92 g of polyethylene glycol 4000 instead of polyethylene glycol 6000 to prepare 100 g of a topical powder composition.

Example 5

30 g of polyethylene glycol 600.0, 65 g of talc, 2 g of Aerogel 200 and 3 g of DBcAMP were mixed and 60 g of the mixture was put in a sugar coating pan. The pan was heated at 75° C. in a water bath and was rotated to prepare granules. When the granulation was finished, granules were rotated at room temperature to cool, thereby obtaining a granular topical powder composition.

Test Example 1

Stability Test

The ointment obtained in the Comparative Example and the topical powder compositions obtained in Examples 1 to 4 were charged in bottles, and a they were kept at 40° C. After one month, DBcAMP was determined by high performance liquid chromatography. The results are shown in Table 1.

TABLE 1

Stability Test Results of DBcAMP (against initial value (%))

| | DBcAMP amount (%) |
|---|---|
| Com. Example | 82.0 |
| Example 1 | 96.9 |
| Example 2 | 95.0 |
| Example 3 | 93.0 |
| Example 4 | 95.7 |

It is readily understood from Table 1 that any topical powder compositions according to the present invention exhibited better stability compared with the comparative ointment.

Test Example 2

Four male SD rats (weight of 250 to 300 g) were used as a group. The abdominal hair was removed, and the rat was fixed on the board under pentobarbital anesthesia. At the skin of the hair-removed part, the stratum corneum was removed from the test site by stripping 20 times with an adhesive tape. An acrylic resin cell-having an internal diameter of 3 cm was stuck in a dosing part using a cyanoacrylate adhesive. Soon after 1 g of each preparation (30 mg of DBcAMP) was dosed in the cell, the upper part of the cell was sealed with a paraffin film. The blood was collected from the jugular vein of 0.5, 1, 2, 4 and 8 hours after the dosage, and the plasma was collected by centrifugation. The amount of the DBcAMP in the plasma was determined by high performance liquid chromatography. The results are shown in Table 2. It is apparent from Table 2 that as compared with the ointment, DBcAMP was gradually absorbed into the system through the skin from the topical powder compositions. Depending on the kind of the water-absorptive powdery material and the powdery material having a low melting point, various topical powder compositions can be prepared. Using such compositions, it can be controlled to release the cyclic AMP derivative gradually or quickly.

TABLE 2

DBcAMP concentration in plasma after dose (average of 4 rats, unit: μg/ml)

| | 0.5 hr | 1 hr | 2 hr | 4 hr | 8 hr |
|---|---|---|---|---|---|
| Com. Example | 0.28 | 0.53 | 1.50 | 3.48 | 3.43 |
| Example 1 | 0.05 | 0.15 | 0.35 | 0.52 | 1.04 |
| Example 4 | 0.13 | 0.25 | 0.51 | 0.82 | 0.91 |
| Example 5 | 0.38 | 0.57 | 0.81 | 2.44 | 3.17 |

What is claimed is:

1. A topical powder composition, comprising a cyclic AMP derivative and a water-absorptive powdery material, wherein said cyclic AMP derivative is selected from the group consisting of $N^6$-monoacyladenosine-3',5'-cyclic phosphoric acid, 2'-O-monoacyladenosine-3',5'-cyclic phosphoric acid, $N^6$,2'-O-diacyladenosine-3',5'-cyclic phosphoric acid, 8-mercapto-$N^6$-monoacyladenosine-3',5'-cyclic phosphoric acid, 8-mercapto-2'-O-monoacyladenosine-3',5'-cyclic phosphoric acid 8-mercapto-$N^6$,2'-O-diacyladenosine-3',5'-cyclic phosphoric acid, 8-lower alkylthio-$N^6$-monoacyladenosine-3',5'-cyclic phosphoric acid, 8-lower alkylthio-2'-O-monoacyladenosine-3',5'-cyclic phosphoric acid, 8-lower alkylthio-$N^6$,2'-O-diacyladenosine-3',5'-cyclic phosphoric acid, 8-benzylthio-$N^6$-monoacyladenosine-3',5'-cyclic phosphoric acid, 8-benzylthio-2'-O-monoacyladenosine-3',5'-cyclic phosphoric acid, 8-benzylthio-$N^6$,2'-O-diacyladenosine-3',5'-cyclic phosphoric acid, 8-amino-$N^6$-monoacyladenosine-3',5'-cyclic phosphoric acid, 8-amino-2'-O-monoacyladenosine-3',5'-cyclic phosphoric acid, 8-amino-$N^6$,2'-O-diacyladenosine-3',5'-cyclic phosphoric acid, 8-hydroxy-$N^6$-monoacyladenosine-3',5'-cyclic phosphoric acid, 8-hydroxy-2'-O-monoacyladenosine- 3',5'-cyclic phosphoric acid, 8-hydroxy-$N^6$,2'-O-diacyladenosine-3',5'-cyclic phosphoric acid, 8-chloro-$N^6$-monoacyladenosine-3'-5'-cyclic phosphoric acid, 8-chloro-2'-O-monoacyladenosine-3',5'-cyclic phosphoric acid, 8-chloro-$N^6$,2'-O-diacyladenosine-3',5'-cyclic phosphoric acid, 8-bromo-$N^6$-monoacyladenosine-3',5'-cyclic phosphoric acid, 8-bromo-2'-O-monoacyladenosine-3',5'-cyclic phosphoric acid, 8-bromo-$N^6$,2'-O-diacyladenosine-3',5'-cyclic phosphoric acid, 8-benzylthioadenosine-3',5'-cyclic phosphoric acid, $N^6$-lower alkyl-8-benzylthioadenosine-3',5'-cyclic phosphoric acid, and 8-mercaptoadenosine-3',5'-cyclic phosphoric acid, and said water-absorptive powdery material is selected from the group consisting of sucrose, starch, pectin, gelatin, sodium alginate, methylcellulose, hydroxypropylcellulose, carboxymethylcellulose, polyvinyl alcohol, polyvinyl pyrrolidone, carboxyvinyl polymer, sodium polyacrylate, and polyethylene glycol, which is prepared by a process comprising blending said cyclic AMP derivative, a powdery material having a low melting point and said water-absorptive powdery material to obtain a mixture, and then, heating with fluidizing said mixture at a temperature higher than the melting point of said powdery material having a low melting point to form granules, wherein said powdery material having a low melting point is selected from the group consisting of waxes, hydrocarbons, fatty acids, fatty acid esters, polyethylene glycols, polyhydric alcohols, higher alcohols, sugar alcohols, and surfactants.

* * * * *